(12) United States Patent
Perry, Jr. et al.

(10) Patent No.: US 11,042,169 B2
(45) Date of Patent: Jun. 22, 2021

(54) METHOD AND APPARATUS FOR CONTROLLING THE FLOW RATE OF FLUID DISCHARGE

(71) Applicant: BreezzAngel, LLC, New Orleans, LA (US)

(72) Inventors: Kenneth Paul Perry, Jr., Youngsville, LA (US); Tonia Dandry Aiken, New Orleans, LA (US); James Beam Aiken, New Orleans, LA (US); Tina Dandry Mayes, Marrero, LA (US)

(73) Assignee: SAFEPUSH, LLC, Marrero, LA (US)

( * ) Notice: Subject to any disclaimer, the term of this patent is extended or adjusted under 35 U.S.C. 154(b) by 0 days.

(21) Appl. No.: 15/901,305

(22) Filed: Feb. 21, 2018

(65) Prior Publication Data

US 2018/0239370 A1 Aug. 23, 2018

Related U.S. Application Data

(60) Provisional application No. 62/461,997, filed on Feb. 22, 2017.

(51) Int. Cl.
| | |
|---|---|
| *G05D 7/01* | (2006.01) |
| *A61M 5/31* | (2006.01) |
| *A61M 39/24* | (2006.01) |
| *F16K 15/02* | (2006.01) |
| *F16K 15/04* | (2006.01) |

(52) U.S. Cl.
CPC ......... *G05D 7/0133* (2013.01); *A61M 5/3134* (2013.01); *A61M 39/24* (2013.01); *A61M 2005/3131* (2013.01); *A61M 2039/242* (2013.01); *A61M 2039/248* (2013.01); *F16K 15/026* (2013.01); *F16K 15/044* (2013.01); *Y10T 137/7873* (2015.04); *Y10T 137/7927* (2015.04)

(58) Field of Classification Search
CPC ... G05D 7/0133; A61M 5/3134; A61M 39/24; A61M 2039/242; A61M 2039/248; Y10T 137/7873; Y10T 137/7838; Y10T 137/7927; F16K 15/026; F16K 15/044
See application file for complete search history.

(56) References Cited

U.S. PATENT DOCUMENTS 2,307,949 A * 1/1943 Phillips ................ G05D 7/0133
  137/498
2,699,179 A * 1/1955 Hansen ................ G05D 7/0133
  137/539

(Continued)

OTHER PUBLICATIONS

PCT International Search Report and Written Opinion dated Jun. 22, 2018.

*Primary Examiner* — Marina A Tietjen
*Assistant Examiner* — Frederick D Soski
(74) *Attorney, Agent, or Firm* — Ted M. Anthony

(57) ABSTRACT

A method and apparatus for use in controlling a dispensing rate of medication or other substance via a syringe, including, without limitation, into a patient, intravenous line port or heparin lock. A fluid flow rate control apparatus has a housing defining an inner chamber with an inlet port and an outlet port. Sealing seats are formed at or near both the inlet and outlet ports, and a moveable sealing element, such as a ball, can move within the inner chamber between the sealing seats. A spring biases the ball toward the inlet port sealing seat.

4 Claims, 12 Drawing Sheets

(56) References Cited

U.S. PATENT DOCUMENTS

| | | | |
|---|---|---|---|
| 2,999,499 A * | 9/1961 | Willet | A61M 5/1408 137/539 |
| 3,386,470 A * | 6/1968 | Goda | F16K 15/026 137/512 |
| 3,894,556 A * | 7/1975 | Pareja | F16K 15/044 137/539 |
| 4,210,173 A | 7/1980 | Choksi et al. | |
| 4,287,912 A * | 9/1981 | Hewett | F16K 15/044 137/516.27 |
| 4,736,768 A * | 4/1988 | Tsubouchi | B60T 11/232 137/493.3 |
| 4,862,911 A * | 9/1989 | Yie | F04B 53/109 137/454.4 |
| 5,378,229 A * | 1/1995 | Layer | A61M 25/1018 137/512 |
| 5,950,670 A * | 9/1999 | Flaim | B25B 11/005 137/493.8 |
| 6,045,759 A * | 4/2000 | Ford | G01N 1/312 137/519.5 |
| 6,244,295 B1 * | 6/2001 | Bartussek | B60T 8/341 137/539 |
| 9,163,618 B2 * | 10/2015 | Wikfors | F04B 11/0075 |
| 2006/0117525 A1 * | 6/2006 | Juntunen | F16K 15/044 16/52 |
| 2007/0093764 A1 * | 4/2007 | Guerrero | A61M 5/1408 604/284 |
| 2007/0276323 A9 | 11/2007 | Matsuura et al. | |
| 2010/0116364 A1 * | 5/2010 | Koyama | B60T 17/04 137/535 |
| 2012/0024987 A1 | 2/2012 | Nägele Nacken | |
| 2015/0219234 A1 * | 8/2015 | Hobmeyr | F16K 15/044 251/337 |
| 2015/0226345 A1 * | 8/2015 | Hartmann | F16K 15/044 137/539 |
| 2017/0138490 A1 * | 5/2017 | Haeusser | F04B 53/1002 |

* cited by examiner

METHOD AND APPARATUS FOR CONTROLLING THE FLOW RATE OF FLUID DISCHARGE

BACKGROUND OF THE PRESENT INVENTION

1. Field of the Invention

The present invention pertains to a method and apparatus for controlling a dispensing rate of fluid (such as, for example, liquid medication) via a syringe, including, without limitation, into an intravenous (IV) line port. More particularly, the present invention pertains to a method and apparatus for regulating the rate of infusion of certain drugs and medications into a patient intravenous line port or heparin lock.

2. Brief Description of the Prior Art

It is frequently beneficial in many different industries and applications to control or regulate fluid flow rate in order to achieve desired system results. One such application is the medical treatment of patients. Although specific situations can vary, one particular medical application where fluid flow rate must be carefully regulated is the administering of drugs and other liquid medicaments to patients.

During emergency events and, in particular, when critical care medications are being administered, injury or death may occur to a patient if medications are administered at a rate higher than prescribed. Conventional devices to regulate dispensing rates exist in various modalities; however, such conventional devices are typically large, expensive, and difficult and time consuming to program. Such conventional devices frequently do not function properly, and are generally not designed to operate in the fast-paced environment of emergency rooms and other healthcare facilities.

Check valves are one type of fluid flow control device commonly used in the medical industry. Generally, a conventional check valve is a device that allows fluid flow in one direction but prevents fluid flow in an opposite direction. Such conventional check valves are pressure-driven devices that are not able to effectively regulate fluid flow rate. Although many different types of check valves exist, one common version comprises a ball that is biased (typically by a force generated by a spring) against a seat disposed on a fluid port. Said force biases the ball against said seat, thereby sealing said fluid port and preventing fluid from flowing through said port. In order for fluid to flow through said port, a sufficient force (typically fluid pressure) must act on the ball and overcome the spring force, thereby "pushing" the ball off of the seat and allowing fluid to flow through the port (and around the unseated ball).

The fluid pressure required to initially dislodge said ball from said seat is often referred to as the "cracking pressure" of the valve. Because fluid flow through such a check valve is governed by Poiseuille's Law and Bernoulli's equation, a direct correlation exists between fluid pressure and fluid flow rate—thus, as long as fluid pressure is equal to or greater than the cracking pressure of a check valve, fluid flow though said valve is essentially unrestricted by said valve. As a result, a ball-and-seat type check valve cannot dependably regulate or control fluid flow rate. If, for example, a ball-and-seat check valve would be attached to the output of a syringe with the intention of regulating flow rate of effluent fluid from said syringe, the effluent fluid flow rate would simply increase in direct proportion to the increase in said fluid pressure as the syringe plunger is pressed with more force.

Another type of check valve is a diaphragm check valve. Such diaphragm check valves are generally constructed from an elastomeric membrane having a slit or aperture to permit fluid flow in one or both directions. As with other check valves, a "cracking pressure" must be achieved before fluid flow can commence across the membrane. However, like other types of check valves, fluid flow rate across the diaphragm is governed by Bernoulli's equation. Thus, as with other check valves, fluid flow is proportional to fluid pressure. Accordingly, such diaphragm check valves are not well suited to control or regulate fluid flow, such as fluid effluent discharged from the outlet of a syringe.

Orifice plates, also known as orifice valves or restriction plates, are also used to control fluid flow. However, for an orifice plate to predictably regulate or control fluid flow and yield a desired output flow rate, the fluid viscosity and fluid pressure must be known and constant, with the orifice sized accordingly. Depending on the length of the orifice valve, a change in fluid pressure can affect the output flow rate of the device. For example, an orifice valve may be used to regulate fluid flow when used in conjunction with output effluent from an intravenous ("IV") bag positioned at an elevated height above the orifice valve. Because head pressure generated by fluid in the IV bag is generally very close to constant, the orifice valve can be used to reliably regulate fluid flow. However, when attached to the fluid discharge outlet of a syringe (which will typically generate varying output fluid pressure due to change in force applied to the syringe plunger), an orifice valve generally cannot dependably regulate the fluid output from a syringe and into a patient.

One method commonly used to regulate infusion rates in medical and laboratory applications is by use of specialized infusion equipment known as a syringe pump, infusion pump, or syringe driver. Such devices are generally powered (typically electrically powered) devices that are designed to receive a pre-loaded syringe. The devices administer fluids—such as drugs or medicaments—from said pre-loaded syringe at a predetermined, programmable flow rate set by an operator, such as a doctor, nurse or other health care provider. Unfortunately, use of such devices is generally time consuming and requires specialized training. For example, in most hospital settings, a doctor must first request or requisition such an infusion device from the hospital equipment control room. Once an infusion device is received in an operating room, a clinician must correctly install one or more pre-loaded syringes into the infusion device. The effluent output flow rate must be programmed into the infusion device by a skilled clinician trained in the use of the device.

Such infusion devices are not well-suited for use in emergency rooms or critical care facilities. The quick pace and frequently unpredictable nature of such environments necessitates quick access to, and reliable control of, infusion of desired medications to patients. The time required to obtain such an infusion device, fit the device with at least one pre-loaded syringe, and correctly program the infusion device all negatively impact the quality of care delivered to a patient in an emergency. Further, empirical data shows that errors occur frequently when improper flow rates are programmed into such infusion devices.

Because a simple-to-use, portable, inexpensive, and readily accessible device for predictably regulating the flow rate of critical care medication dispensed to a patient is currently not available, clinicians typically administer such medication while watching a clock or wristwatch to estimate flow rate of effluent discharged from a syringe. This method is subject to inaccuracy and requires a doctor or healthcare professional to direct his or her attention away from a patient in order to monitor the flow from the syringe and simultaneously the time passing on a wristwatch or clock. Moreover, vital signs of the patient must be monitored while administering the medication to prevent detrimental effects and to monitor beneficial results. This process of attempting to simultaneously monitor patient vital signs, a watch or clock, and the flow rate from a syringe creates a high probability for errors in flow rate estimation and missing of signs or symptoms exhibited by a patient. Studies have shown that such errors, which can frequently prove to be deadly, predominantly result from administering medication to a patient at a flowrate that is higher than desired.

Some medications can be given as a "bolus"—that is, such medicines can be injected into a patient's vein without regard to fluid flow rate. Conversely, there are other critical care medications that must be administered as a dose over unit time; many of these drugs are administered over a predetermined time period (typically three to five minutes).

Given these differing times of administrations between critical care medications, there exists a time of administration gap in critical care medicine in the administering of critical care medications. This gap relates to the period of time (usually 3-5 minutes), which is the time of administration gap between administering mediations as a bolus and giving the drugs over a longer prescribed period of time that would be more conducive to a syringe or infusion pump.

Thus, there is a need for a reliable, effective, inexpensive and user-friendly means for controlled fluid flow rate regulation, particularly (but not exclusively) during this time of administration gap. A clinician should be able to beneficially avoid delay and safely administer medicine at a desired flow rate, while simultaneously monitoring a patient receiving such medicine.

SUMMARY OF THE PRESENT INVENTION

The present invention comprises a method and apparatus for controlling the dispensing flow rate of medication or other fluids from devices including, but not limited to, pumps, syringes, and intravenous lines. The method and apparatus of the present invention provide a modality to regulate the infusion rate or flow rate that is not dependent on a specific administration technique. By way of illustration, but not limitation, hospital emergency and trauma personnel, and paramedics can beneficially utilize the method and apparatus of the present invention in an emergency room or similar setting. However, the method and apparatus of the present invention can also be employed anywhere that a fluid flow rate must be controlled or in applications that use flow rate to regulate a related function of another device.

Certain medical situations occur in remote or undeveloped locations where access to electricity and/or infrastructure is not present (such as, for example, on a battlefield or during pre-hospital EMS care). The present invention—which is small, disposable, lightweight and portable—can work without electricity or other external power source, and is highly desirable and effective. Further, the apparatus of the present invention can quickly and simply attach to existing, standard equipment such as conventional syringes, IV hoses and manifolds without modification or specialized equipment.

The present invention regulates fluid flow rate by placing a configurable restriction into a fluid flow stream. Such restriction can be, without limitation, in the form of a ball and seat, a flapper valve, or a diaphragm. Although the flow regulating section of the device can be made of various materials and in various configurations, preferred configurations are described herein.

In a preferred embodiment, a fluid flow rate control apparatus of the present invention comprises a housing defining an inner chamber, typically in the form of a through bore, having an inlet port and an outlet port, with a sealing seat on each of said inlet and outlet ports. A moveable sealing element such as a ball, is free to move within said inner chamber between said seats. Said seat on said inlet port faces toward said ball and in the direction of fluid flow, while said seat on the outlet port of the chamber also faces said ball and generally in the opposite direction as said fluid flow. Force (such as from a bias spring or gravity) acts on said ball, biasing said ball toward said seat disposed at said inlet port.

Fluid is introduced through said inlet port into said inner chamber. Said fluid passes through said inlet port, through said inner chamber and out of said outlet port. Fluid flow rate passing through said inner chamber is regulated or controlled; as discussed in more detail herein, said fluid flow rate never exceeds a predetermined maximum flow rate regardless of fluid pressure entering said inner chamber.

BRIEF DESCRIPTION OF THE DRAWINGS

The foregoing summary, as well as any detailed description of the preferred embodiments, is better understood when read in conjunction with the drawings and figures contained herein. For the purpose of illustrating the invention, the drawings and figures show certain preferred embodiments. It is understood, however, that the invention is not limited to the specific methods and devices disclosed in such drawings or figures.

DETAILED DESCRIPTION OF A PREFERRED EMBODIMENT

In a preferred embodiment, the present invention comprises a relatively small, compact disposable, lightweight and portable fluid flow rate control apparatus capable of functioning without electricity or other external power source. The apparatus of the present invention can quickly and simply attach to existing equipment (including, without limitation, medical dispensing equipment) such as conventional syringes, IV hoses and manifolds without modification or specialized tools or training. Further, said fluid flow control apparatus can restrict or control fluid flow to desired and substantially constant flow rates; by way of illustration, but not limitation, the fluid flow control apparatus of the present invention can provide a predetermined and substantially constant maximum effluent or output flow rate from a conventional syringe or other medical dispensing device. For example, said output flow rate can be regulated at the equivalent of 1 ml, 2 ml, 5 ml or 10 ml per minute, or practically any other desired or predetermined output flow rate.

Generally, the fluid flow rate control apparatus of the present invention comprises a housing defining an inner chamber or internal bore having an inlet port and an outlet port. A sealing seat is disposed on each of said inlet and outlet ports; each of said seats faces inward toward said inner chamber/internal bore. A moveable sealing element such as a ball is disposed within said inner chamber or internal bore and is free to move within said inner chamber between said seats. Force (such as from a bias spring or gravity) acts on said ball, biasing said ball toward said inlet port seat. Fluid is introduced through said inlet port into said inner chamber. Said fluid passes through said inlet port, through said inner chamber/bore and out of said outlet port. Fluid flow rate passing through said inner chamber is regulated and/or controlled; said fluid flow rate never exceeds a predetermined maximum flow rate regardless of fluid pressure of said fluid entering said inner chamber.

Figure 1:
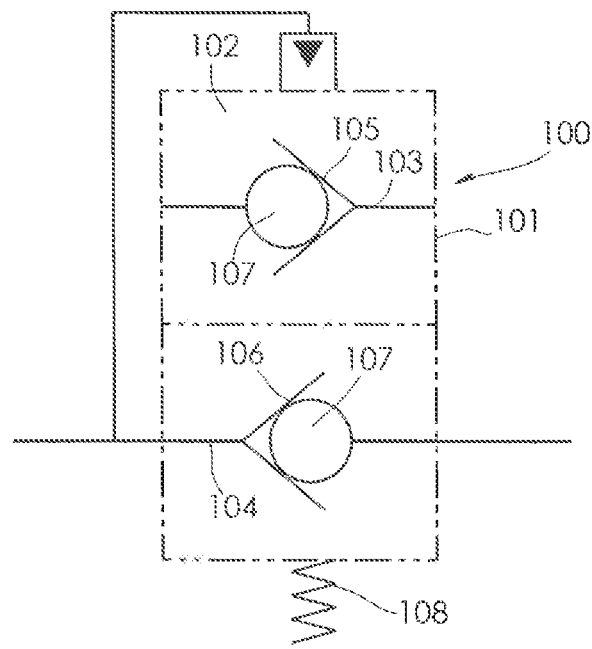
FIG. 1 depicts a schematic diagram of a flow fuse circuit of a fluid flow rate control apparatus of the present invention.

Referring to the drawings, FIG. 1 depicts a schematic diagram of a flow fuse circuit 100 of a fluid flow rate control apparatus of the present invention. Unlike a conventional check valve, the fluid flow rate control apparatus of the present invention does not rely solely on fluid pressure to regulate flow rate. Instead, flow of fluid across a sealing element, such as a ball or flapper, causes a differential pressure to exist across said sealing element. When said differential pressure reaches a predetermined desired amount, said sealing element blocks (at least temporarily) fluid from flowing through said fluid flow rate control apparatus.

Referring to FIG. 1, housing 101 defines an internal chamber or internal bore 102 having an outlet port 103 and an inlet port 104. A sealing seat 105 is disposed on outlet port 103, while sealing seat 106 is disposed on inlet port 104; seats 105 and 106 face inward toward said internal bore 102. A moveable sealing ball 107 is disposed within said internal bore 102 and is free to move within said internal bore 102 between said seats 105 and 106, but is normally biased against inlet seat 106 by compression spring 108. As fluid flow enters internal bore 102 through inlet port 104, fluid velocity through said internal bore 102 increases. Said fluid shifts ball 107 toward seat 105 disposed at outlet port 103, while compression spring 108 biases said ball 107 away from or off of said seat 105; said spring 108 provides resistive force to keep ball 107 from fully contacting seat 105 and blocking outlet port 103. Ball 107 slows the fluid flow until the bias force of spring 108 is overcome, thereby allowing ball 107 to contact seat 105 and form a fluid pressure seal which, in turn, interrupts fluid flow through said outlet port 103.

In a preferred embodiment, the fluid flow rate control apparatus of the present invention should be sufficiently small to conveniently fit within a utility cart, sometimes called a "crash cart", used in an operating room, or in a bag used for EMS applications. Further, in said preferred embodiment, a clinician should be able to simply attach the current invention to the output port of a syringe or other device using a conventional "Luer lock" or "Luer taper" fitting connection that is well known in the industry. In this configuration, specialized equipment or training is not required and the invention can be operationally connected or disconnected without use of specialized tools. The Luer adapter readily attaches to standard medical ports, IV tubing, manifolds and/or other conventional equipment.

Figure 2:
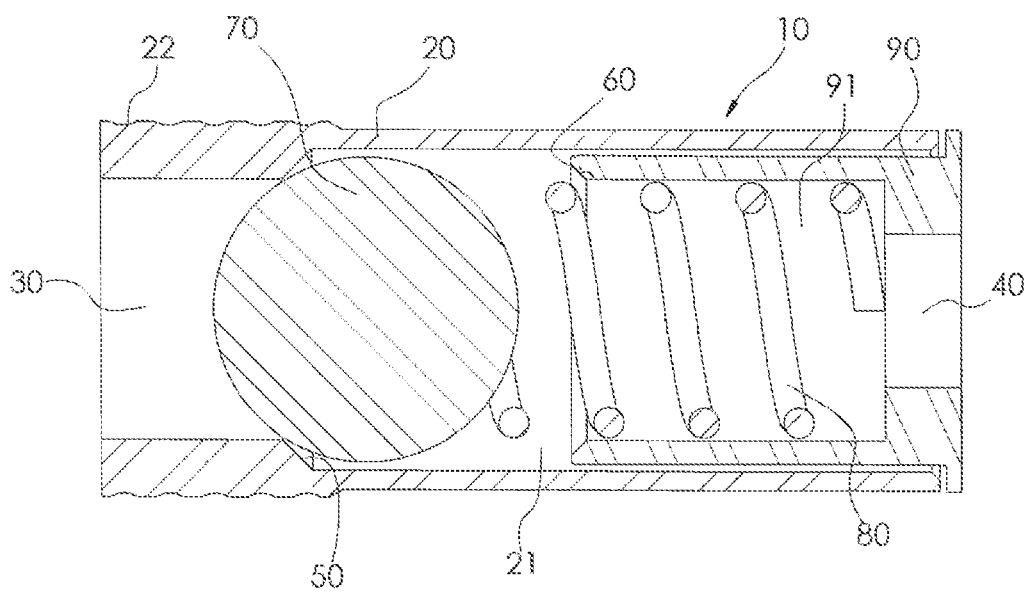
FIG. 2 depicts a side sectional view of a fluid flow rate control apparatus of the present invention with a ball against an inlet port seat.
Figure 3:
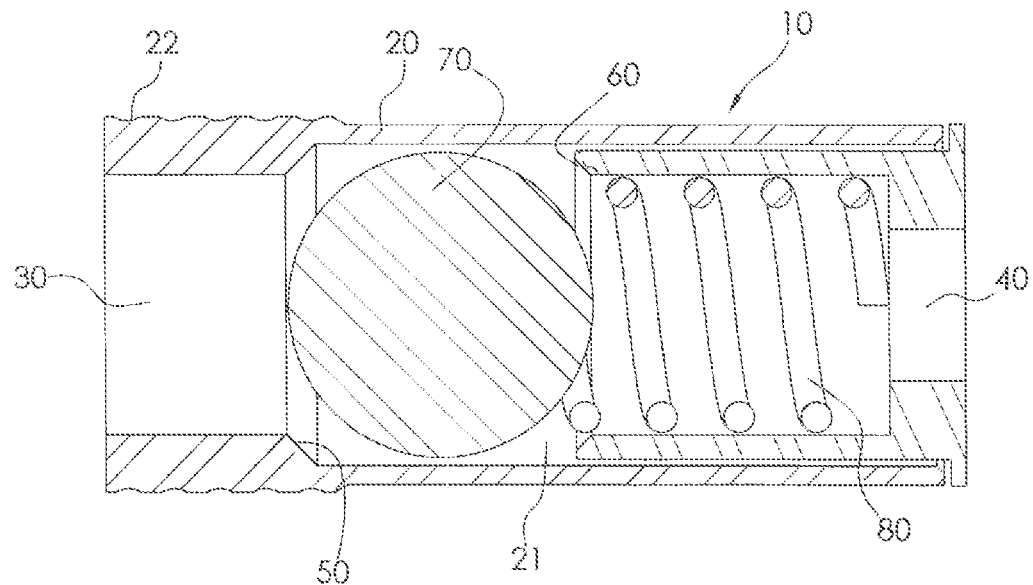
FIG. 3 depicts a side sectional view of a fluid flow rate control apparatus of the present invention with a ball removed from an inlet port seat.
Figure 4:
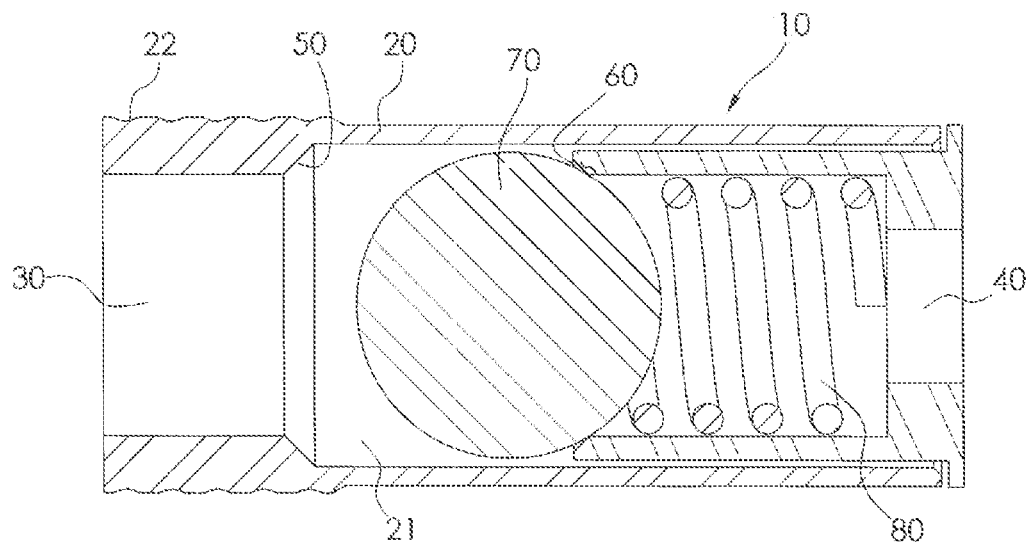
FIG. 4 depicts a side sectional view of a fluid flow rate control apparatus of the present invention with a ball positioned on an outlet port seat.

FIGS. 2 through 4 depict sequential side sectional views of a fluid flow rate control apparatus 10 of the present invention during the regulation of fluid flow through said apparatus 10. FIG. 2. depicts said fluid flow rate control apparatus 10 with a ball against an inlet port seat, while FIG. 3 depicts said fluid flow rate control apparatus 10 with a ball removed from an inlet port seat. FIG. 4 depicts a side sectional view of said fluid flow rate control apparatus 10 a ball positioned against an outlet port seat.

As depicted in FIGS. 2 through 4, fluid flow rate control apparatus 10 comprises housing 20 having a through bore—defining an internal chamber 21—having an inlet port 30 and an outlet port 40; said inlet port 30 and outlet port 40 extend into said inner chamber 21. In a preferred embodiment, said inner chamber 21 is formed by a flow bore extending through housing 20. Housing 20 can include Luer lock connection threads, ribs 22 for frictional attachment to other components, or other desired connection profile for operationally attaching said fluid flow rate control apparatus 10 to a mating component.

In a preferred embodiment, inlet sealing seat 50 is disposed at or near inlet port 30, while end member 90 is operationally attached to housing 20. End member 90 has inner bore 91 in fluid communication with outlet port 40 and defines outlet sealing seat 60 that is disposed at or near said outlet port 40. Inlet sealing seat 50 and outlet sealing seat 60 both face generally inward in opposing orientation, facing toward said inner chamber 21. A moveable sealing ball 70 is disposed within said inner chamber 21 of housing 20, and is generally free to move within said inner chamber 21 between said inlet sealing seat 50 and outlet sealing seat 60.

Referring to FIG. 2, sealing ball 70 can be disposed against inlet sealing seat 50 to form a fluid pressure seal and prevent fluid from exiting inner chamber 21 through inlet port 30 (that is, fluid flowing in a direction opposite from the desired direction). As fluid flow enters inner chamber 21 of housing 20 through inlet port 30, fluid velocity through said inner chamber 21 increases. Said flowing fluid shifts ball 70 generally in the direction of outlet sealing seat 60. Compression spring 80 is disposed within inner bore 91 of end member 90 and biases said ball 70 away from or off of said outlet sealing seat 60; said spring 80 provides resistive force to bias said ball 70 away from fully contacting said outlet sealing seat 60 and blocking outlet port 40.

Referring to FIG. 3, fluid (such as from a conventional syringe or other fluid source) flows through inlet port 30 and into inner chamber 21. Said fluid flows against and around ball 70, through inner chamber 21, and exits said outlet port 40. In this configuration, said fluid imparts force acting on ball 70 generally in the direction of said fluid flow and said outlet port 40. The dimensions and characteristics of ball 70, physical characteristics of said fluid, housing 20 and inner chamber 21, and fluid flow rate around ball, collectively affect the amount of force that said fluid imparts on said ball 70. When the flow rate of the fluid passing around said ball 70 remains within a predetermined acceptable designed flow rate, ball 70 remains positioned between inlet sealing seat 50 and outlet sealing seat 60, thereby allowing continuous or uninterrupted fluid flow through said fluid flow rate control apparatus 10.

Referring to FIG. 4, as fluid flow rate increases, the fluid passing through inner chamber 21 and around ball 70 imparts greater force acting on said ball 70. Compression spring 80 acts to resist such fluid force (that is, said spring 80 imparts force in a direction opposite from said fluid flow) and bias said ball 70 away from said outlet seat 60, but becomes more compressed as the fluid force acting on ball 70 increases. Eventually, when a predetermined maximum allowable fluid flow rate is achieved, said fluid force overcomes the force of spring 80 acting on ball 70, thereby allowing ball 70 to contact and engage with outlet seat 60. In one embodiment, said ball 70 forms a fluid pressure seal against said outlet seat 60, thereby blocking or stopping fluid flow around said ball 70, past outlet seat and through said outlet port 40.

In a preferred embodiment, fluid flow rate control apparatus 10 of the present invention is configured so that a predetermined maximum acceptable fluid flow rate through inner chamber 21 creates a predetermined force on ball 70 that compresses spring 80 sufficiently to cause ball 70 to engage with, and seal against, outlet seat 60. In this position, ball 70 greatly completely interrupts fluid flow through fluid flow rate control apparatus 10. Determination of a force imparted on ball 70 by fluid flow rates can be accomplished by adjusting certain design parameters of the apparatus including, but not limited to, inlet port 30 size, outlet port 40 size, compression spring rate and/or other force characteristics of compression spring 80, size of ball 70, and dimensions (including, but not necessarily limited to, length and diameter) of inner chamber 21.

In certain applications, such as when fluid flow rate control apparatus 10 of the present invention is used in connection with the outlet from a conventional syringe, fluid pressure created by a syringe plunger acting on fluid output from said syringe may cause ball 70 to remain seated on outlet seat 60. In this scenario, fluid entering inner chamber 21 can become trapped between said syringe plunger and flow control ball 70 when a predetermined maximum flow rate is achieved and said ball 70 is forced (and forms a fluid pressure seal) against outlet seat 60. If the fluid pressure seal on said syringe plunger is sufficiently tight, and the fluid pressure seal between ball 70 and outlet seat 60 is also sufficiently tight, fluid pressure trapped there between may prevent said ball 70 from eventually unseating from said outlet seat 60.

In order to permit fluid to flow through fluid flow rate control apparatus 10 of the present invention, in a preferred embodiment such fluid pressure acting on ball 70 can be sufficiently relieved for spring 80 to overcome said fluid pressure and effectively push ball 70 off of said outlet port seat. Relief of such fluid pressure is achieved by providing a fluid flow path for a relatively small volume of such fluid to bypass the interface between ball 70 and outlet seat 60. In a preferred embodiment, said path can comprise a separate bleed-off circuit or, alternatively, an "imperfect" surface outlet seat 60 (that is, wherein said outlet seat 60 does not precisely conform to the outer surface of said ball 70, thereby allowing for at least one gap or space between said ball 70 and seat 60).

Figure 5:
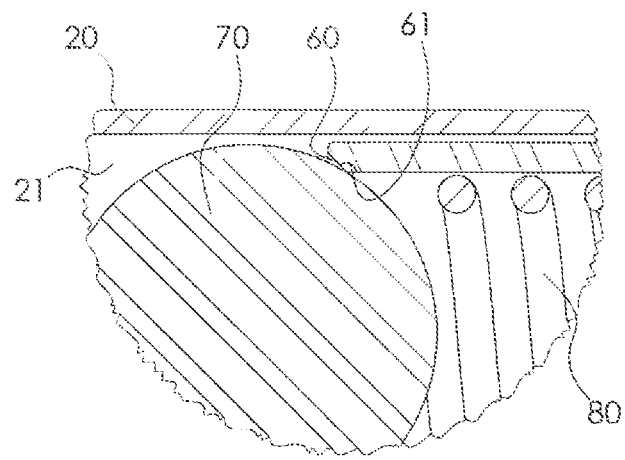
FIG. 5 depicts a detailed sectional view of a portion of the outlet port seat depicted in FIG. 4.
Figure 6:
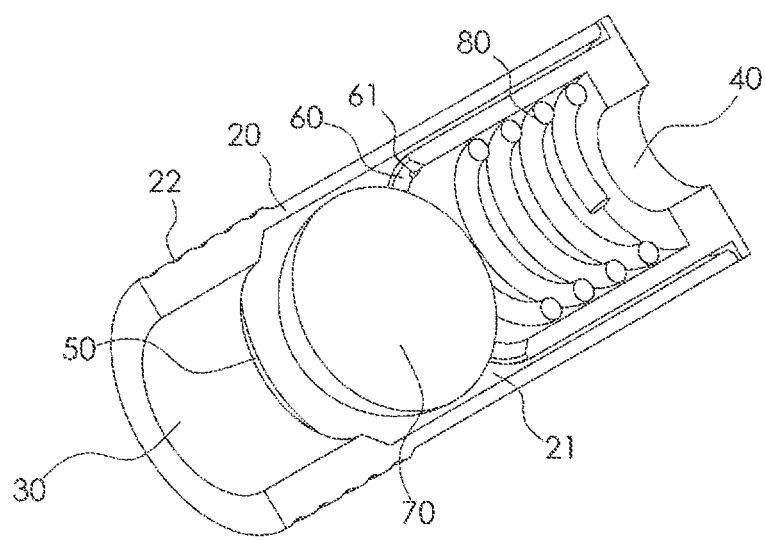
FIG. 6 depicts a sectional perspective view of a fluid flow rate control apparatus of the present invention.

FIG. 5 depicts a detailed sectional view of a portion of outlet seat 60 depicted in FIG. 4, while FIG. 6 depicts a sectional perspective view of a fluid flow rate control apparatus 10 of the present invention including said outlet seat 60. As depicted in FIGS. 5 and 6, a dimple 61 having predetermined dimensions can be disposed on said outlet seat 60. Dimple 61 forms an "imperfection" on the surface of outlet seat 60, preventing ball 70 from fully engaging against seat 60 and forming a complete fluid pressure seal—that is, said dimple 61 creates at least one predetermined gap or space having desired dimensions between said ball 70 and outlet seat 60. Presence of said at least one gap or space allows a predetermined (typically, relatively small) volume of fluid to flow past said ball 70 and outlet seat 60 over a predetermined period of time, thereby allowing some portion of trapped fluid pressure between said syringe plunger and ball 70 to be relieved. Importantly, in a preferred embodiment, such a fluid "leak" only occurs when fluid flow rate passing through inner chamber 21 exceeds a predetermined maximum allowable fluid flow rate (and the corresponding fluid pressure acting on ball 70). In this configuration, fluid flow rate is restricted, but may never be completely interrupted or blocked because some volume of fluid is permitted to bleed through said predetermined gap or space.

In conventional hydraulic applications, hydraulic oil or other power fluid flows from a reservoir to another system component. In order to regulate the flow rate, any "excess"

fluid flow is redirected back into said fluid reservoir. By contrast, particularly in connection with medical applications, such a solution is generally not acceptable when there is no fluid reservoir to receive any excess flow volume. As such, the regulation of fluid flow rate by the fluid flow rate control apparatus 10 of the present invention is achieved without the removal of "excess" fluid volume from the flow stream. In other words, with the present invention, a full volume of fluid or medication that is drawn into a syringe or other device is dispensed to a patient, receptacle or other end point; there is no "reservoir" into which such excess fluid is diverted. As a result, the present invention regulates fluid flow rate by restricting "excess" fluid flow, rather than by diverting some portion of a flow stream into a reservoir or holding chamber.

Figure 7:
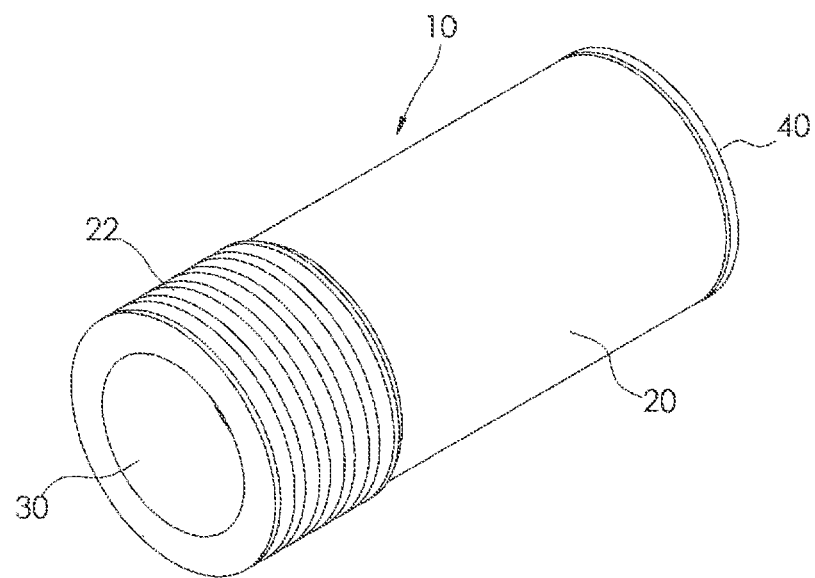
FIG. 7 depicts a perspective view of a fluid flow rate control apparatus of the present invention.

FIG. 7 depicts a perspective view of a fluid flow rate control apparatus 10 of the present invention. Said fluid flow rate control apparatus 10 comprises housing 20 defining an internal bore 21 (not visible in FIG. 7) having an inlet port 30 and an outlet port 40 (not visible in FIG. 7). In a preferred embodiment, said housing 20 can include external ribs 22 or, alternatively, Luer lock connection threads or other desired connection profile for operationally attaching said fluid flow rate control apparatus 10 to a mating component.

Figure 8:
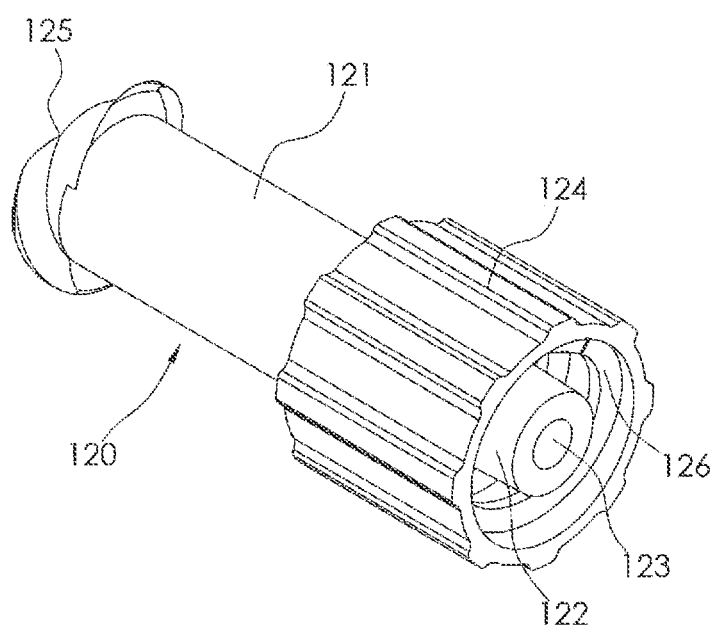
FIG. 8 depicts a perspective view of a fluid flow rate control apparatus of the present invention operationally installed within a Luer lock adapter.

FIG. 8 depicts a perspective view of a fluid flow rate control apparatus of the present invention operationally attached to a Luer lock adapter 120. Said Luer lock adapter 120 generally comprises body section 121 having a first end and a second end. An output nozzle member 122 having a central flow bore 123 is disposed at said first end within a female connection cap member 124 having internal threads or protrusions 126. A barb member 125 is disposed at said second end of said body section 121. In the configuration depicted in FIG. 8, it is to be observed that the portion of Luer lock adapter 120 in the vicinity of barb 125 generally comprises a conventional "female" Luer lock connection member, while the portion in the vicinity of components 122, 123, 124 and 126 generally comprises a "male" Luer lock connection member. However, it is also be observed that said connection members are illustrative only, and other connection means or configurations can be employed to permit quick and efficient connection with other mating components without departing from the scope of the present invention.

Figure 9:
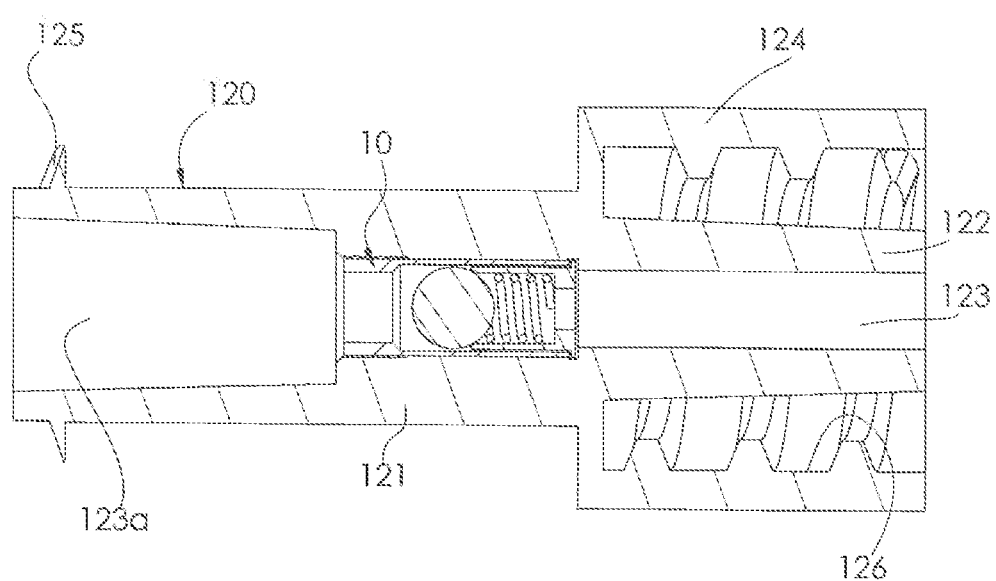
FIG. 9 depicts a side sectional view of a fluid flow rate control apparatus of the present invention installed within a Luer lock adapter (such as may be used, for example, with an IV tube).

FIG. 9 depicts a side sectional view of a fluid flow rate control apparatus 10 of the present invention installed within a central flow bore 123 of said Luer lock adapter 120 (such as may be used, for example, with an IV tube). Said Luer lock adapter 120 generally comprises body section 121 having output nozzle member 122 disposed at one end, and barb member 125 disposed at the opposite end of said body section. Female connection cap member 124 having internal threads or protrusions 126 is disposed around said nozzle output member 122. In the embodiment of Luer lock adapter 120 depicted in FIG. 9, section 123a of central through bore 123 can have a greater internal diameter than at said nozzle output member 122.

Figure 10:
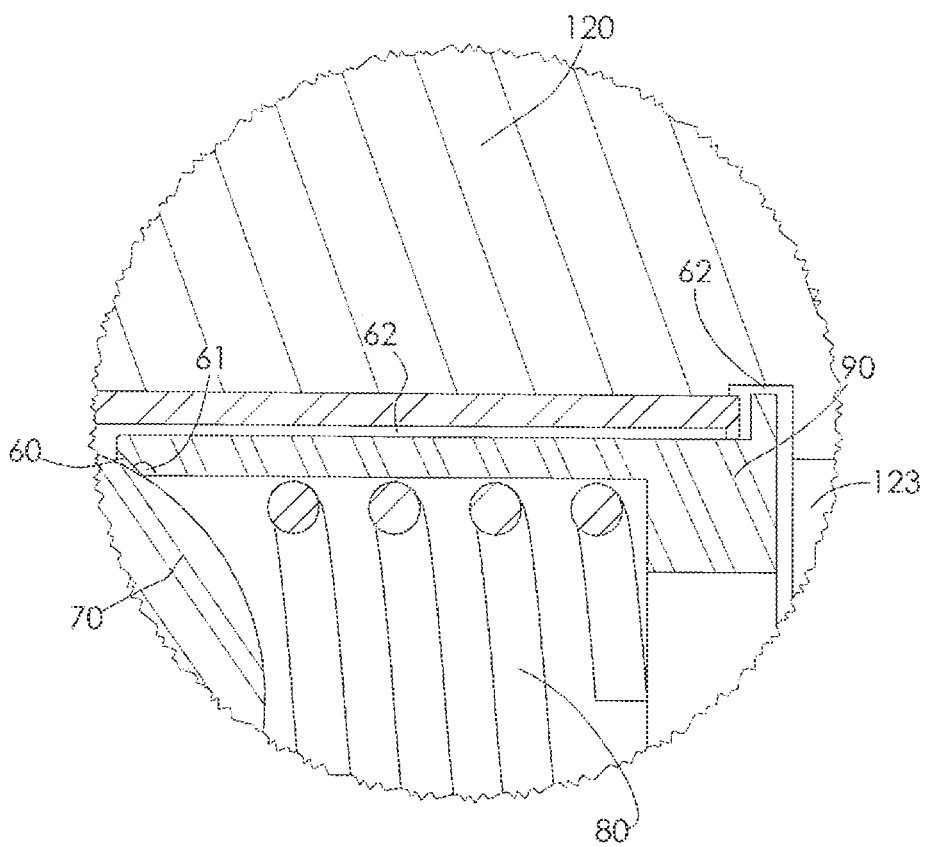
FIG. 10 depicts a detailed view of a portion of a fluid flow rate control apparatus of the present invention depicted in FIG. 9.

FIG. 10 depicts a detailed view of a portion of a fluid flow rate control apparatus 10 of the present invention installed within Luer lock adapter 120. Dimple 61 can be formed on the sealing surface of output seat 60 to allow a relatively small volume of fluid to escape around ball 70 even when said ball 70 is in contact with said outlet seat 60. Additionally, or alternatively, a bleed-off or leak path or channel 62 can be intentionally formed to allow a relatively small amount of fluid to flow out of the apparatus of the present invention even when said ball 70 is in contact with said outlet seat 60.

As depicted in FIG. 10, a flow channel 62 is intentionally created between components of the fluid flow control apparatus 10 of the current invention. A cavity in Luer adapter 120 into which said fluid flow control apparatus 10 is received includes a fluid flow path to allow a relatively small volume of fluid to flow from said fluid flow control apparatus 10 to join with the output flow to relieve fluid pressure. Said relief flow path channel 62 is designed specifically with a very high tolerance and sufficiently close to the outer surface of fluid flow control apparatus 10 to additionally limit the bypass flow and ensure that the overall flow rate exiting the apparatus (and into the patient or other receptacle) does not exceed the desired flow rate due to the inclusion of such bypass fluid in the overall fluid flow rate.

Figure 11:
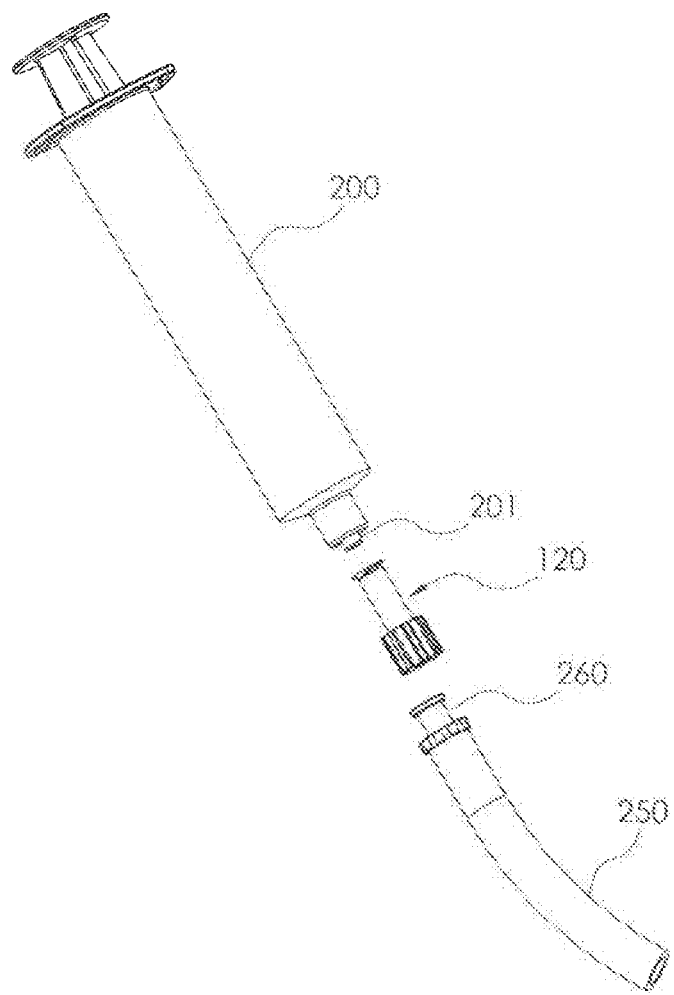
FIG. 11 depicts a side, partially exploded view of a conventional syringe, a male by female Luer adapter including a fluid flow rate control apparatus of the present invention, and a conventional IV tube.

FIG. 11 depicts a side, partially exploded view of a conventional syringe 200, a male by female Luer adapter 120 (including a fluid flow rate control apparatus 10 of the present invention not visible in FIG. 11) and a proximate end of a conventional IV tube 250 having mating adapter 260. As depicted in FIG. 11, Luer adapter 120—as well as a fluid flow rate control apparatus 10 of the present invention contained therein—can be quickly and efficiently installed in sequence between syringe 200 and conventional IV line 250. Said Luer adapter 120 can be operationally attached to the output port 201 of syringe 200. Similarly, said Luer adapter 120 can be operationally attached to IV tube 250 using mating adapter 260.

Figure 12:
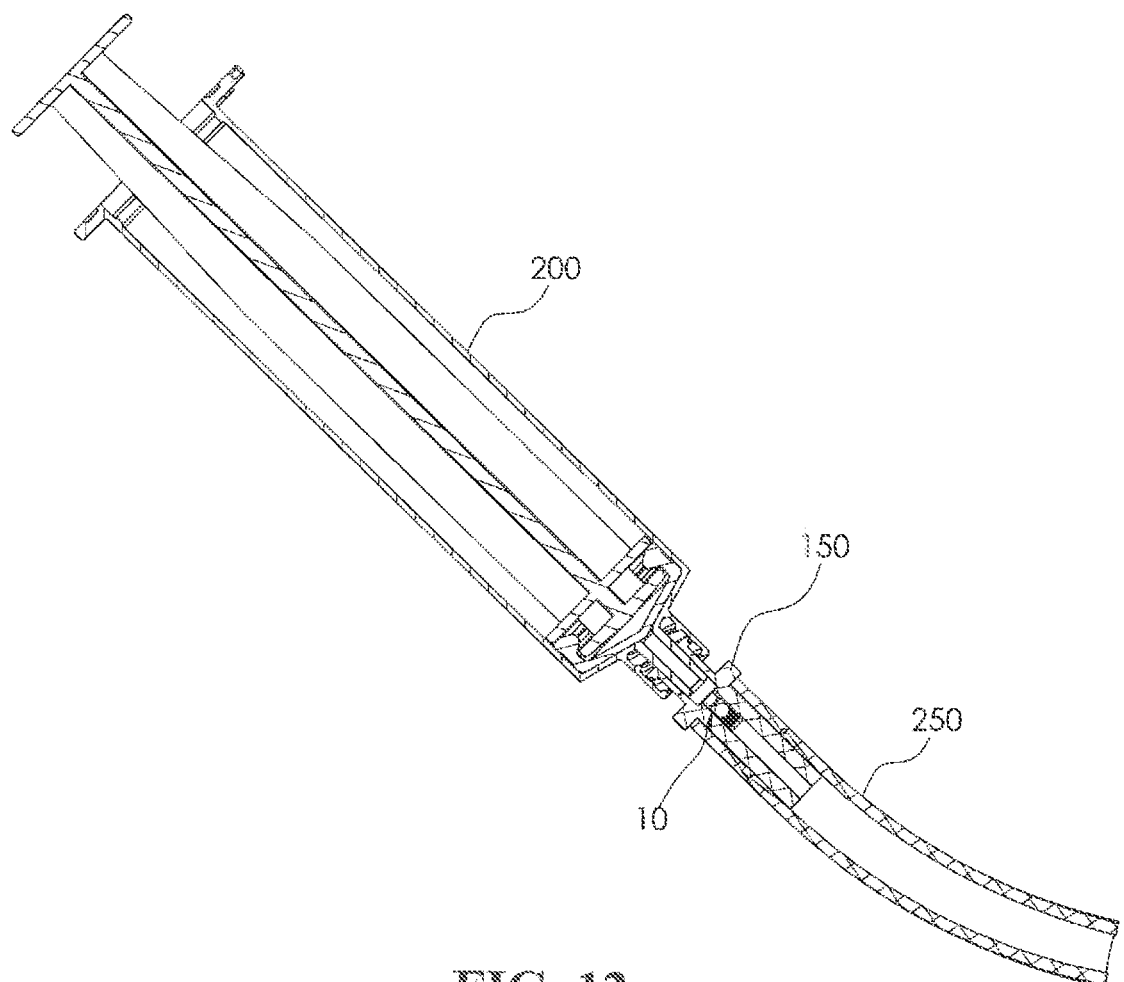
FIG. 12 depicts a side sectional view of a conventional syringe, an IV tube adapter (end connector) of the present invention including a fluid flow rate control apparatus of the present invention, and a conventional IV tube.
Figure 13:
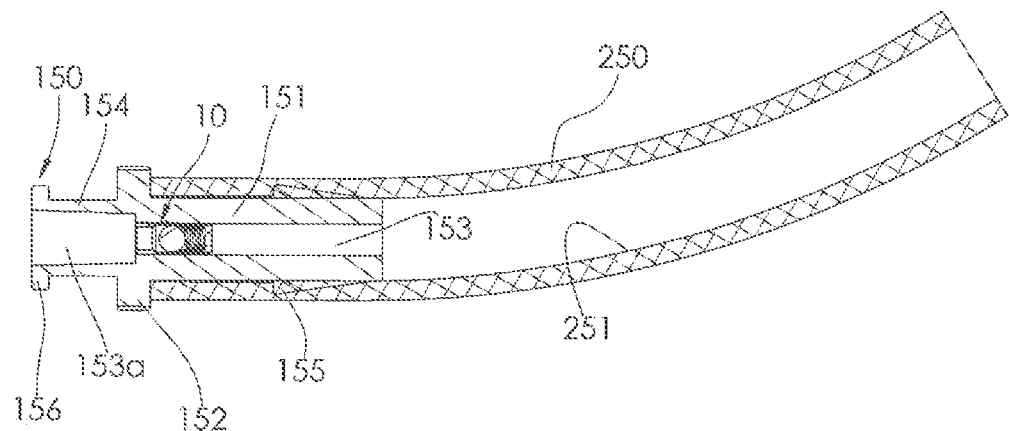
FIG. 13 depicts a side sectional view of a fluid flow rate control apparatus of the present invention installed within an IV tube adapter (end connector) of the present invention operationally attached to a conventional IV or manifold tube.

FIG. 12 depicts a side sectional view of a conventional syringe 200, an IV tube adapter (end connector) 150 of the present invention including a fluid flow rate control apparatus 10 of the present invention, and a conventional IV tube 250. FIG. 13 depicts a side sectional view of a fluid flow rate control apparatus 10 of the present invention installed within said IV tube adapter (end connector) 150 of the present invention operationally attached to a conventional IV or manifold tube 250.

Referring to FIG. 13, IV tube adapter 150 generally comprises body section 151 having barb member 155 disposed at an end of said body section 151. Fluid flow rate control apparatus 10 is received within central through bore 153 of said body section 151. Tube-stop flange member 152 extends radially outward from body section 151 around at least a portion of said body section 151. Further, extension neck 154 having connection flange 156 extends from said body section 151. Section 153a of central through bore 153 corresponding to extension neck 154 can have a greater internal diameter than other sections of said central through bore 153. As depicted in FIG. 13, a portion of body section 151 of IV tube adapter 150 can be received within central bore 251 of IV tube 250. The outer diameter of body section 151 can be beneficially sized and configured (such as, for example, including a gentle taper) to be received within central bore 251 of IV tube 250, while providing a frictional snug fit between said IV tube adapter 150 and IV tube 250. Barb 155 helps to prevent said IV tube adapter 150 from inadvertently dislodging from central bore 251 of IV tube 250.

Figure 14:
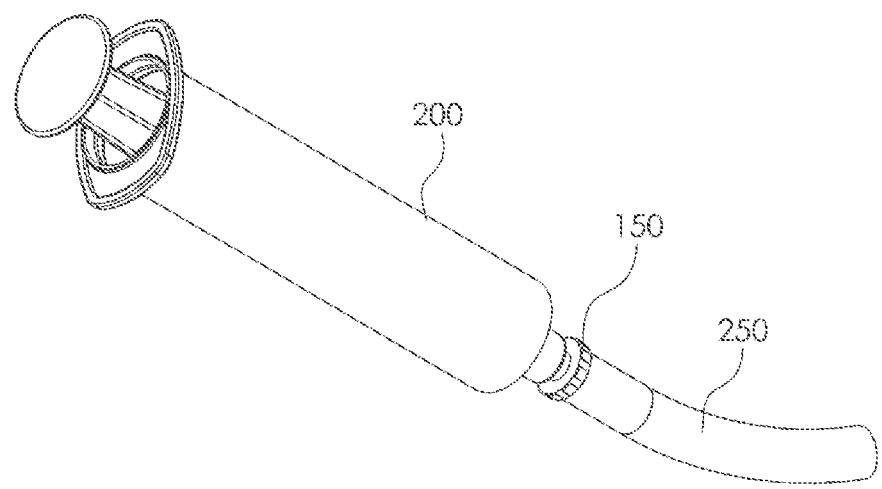
FIG. 14 depicts a perspective view of a fluid flow rate control apparatus of the present invention installed within an IV tube adapter (end connector) of the present invention operationally attached to a conventional IV or manifold tube and a conventional syringe.

FIG. 14 depicts a perspective view of an IV tube adapter (end connector) 150 of the present invention operationally attached between to a conventional IV or manifold tube 250 and a conventional syringe 200. As depicted in FIG. 14, IV tube adapter (end connector) 150—as well as a fluid flow rate control apparatus 10 of the present invention contained therein—can be quickly and efficiently installed in sequence between syringe 200 and conventional IV line 250.

In a preferred embodiment, a flow control apparatus 10 of the present invention can be quickly and efficiently operationally coupled to the output port of a syringe 200 having a desired volume and flow capacity. By way of illustration, but not limitation, said flow control apparatus 10 can be contained within a Luer lock adapter (such as Luer lock adapter 120 depicted in FIGS. 8 through 11), or IV tube adapter (such as IV tube adapter 150 depicted in FIGS. 12 through 14).

Notwithstanding the foregoing, it is to be observed that said flow control apparatus 10 of the present invention can also be included or incorporated within any number of different adapters or couplings having desired dimensions or configurations, and that can be installed downstream of a syringe or other dispensing device, without departing from the scope of the present invention. Unless operational parameters dictate otherwise, in most cases said adapters or couplings (including, without limitation, Luer lock adapter 120 and IV tube adapter 150) comprise relatively small plastic members having appropriate connections to permit quick and efficient operational attachment to said adapter (and the flow control apparatus 10 contained therein) within a flow path downstream of an output port of a syringe.

Furthermore, flow control apparatus 10 of the present invention can be placed or incorporated elsewhere in a fluid circuit, such as between two hoses; in such instances, the flow control apparatus of the present invention can be constructed with opposing hose barbs on each end. It is to be observed that the flow control apparatus of the present invention can also be incorporated into other medical devices where flow controlling capabilities are beneficial to the function of the system such as, for example, medicine ports, IV's and heparin lock systems.

Figure 15:
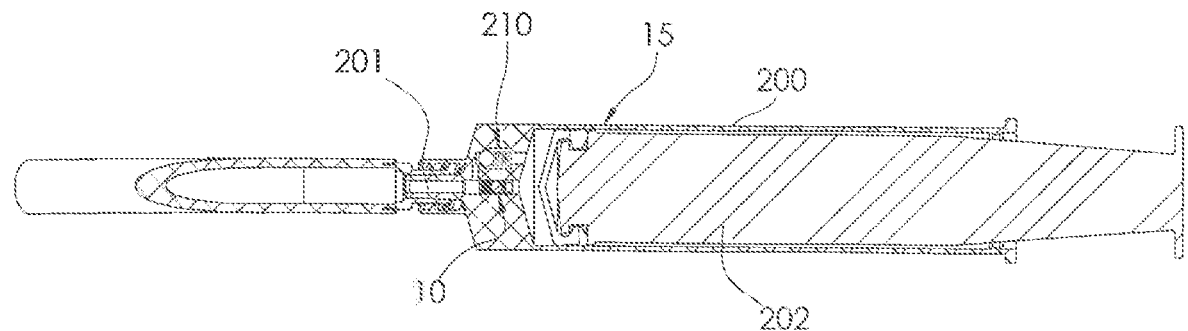
FIG. 15 depicts a side sectional view of a first alternative embodiment fluid flow rate control apparatus of the present invention in a syringe also equipped with a check valve assembly.
Figure 16:
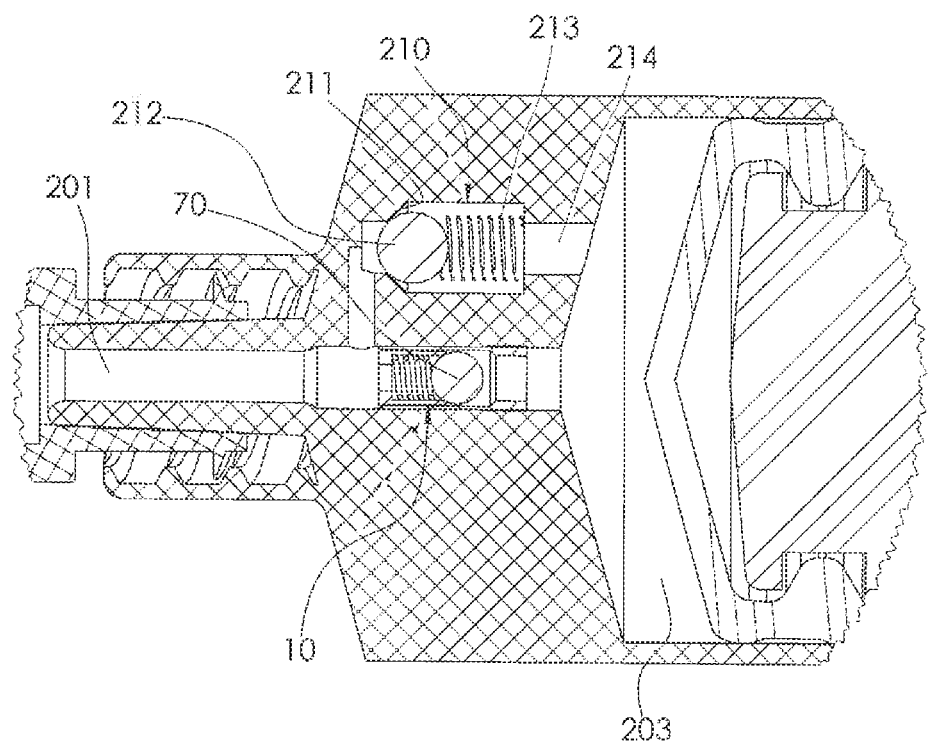
FIG. 16 depicts a detailed sectional view of a portion of the first alternative embodiment depicted in FIG. 15.

FIG. 15 depicts a side sectional view of a first alternative embodiment fluid flow rate control apparatus 15 of the present invention comprising a syringe equipped with a check valve assembly. FIG. 16 depicts a detailed sectional view of a portion of the first alternative embodiment fluid flow rate apparatus 15 depicted in FIG. 15.

In said first alternative embodiment depicted in FIGS. 15 and 16, the present invention generally comprises a syringe 200 having a plunger 202 and a fluid output port 201. A fluid flow control apparatus 10 of the present invention is disposed within the body of syringe 200, between plunger 202 and fluid outlet 201. A second bore or flow channel extends through said syringe body, and a check valve assembly 210 is disposed in said second bore or flow channel, and can be integrally formed within the body of said syringe 200.

Referring to FIG. 16, said check valve assembly 210 comprises an internal seat or sealing surface 211, sealing ball 212, and a compression spring 213; bore 214 extends from the barrel 203 of syringe 200 to fluid outlet 201. First alternative embodiment 15 allows fluid to be drawn into barrel 203 of syringe 200 via channel 214, but prevents said fluid from flowing in an opposite direction (that is, out of barrel 203 through channel 214). Said check valve assembly 210 can comprise different materials, configurations, and sealing systems, but generally allows fluid flow in only a single direction.

In the first alternative embodiment depicted in FIGS. 15 and 16, plunger 202 can be depressed fully into syringe barrel 203 prior to filling said syringe barrel 203 with fluid. Thereafter, a user can connect syringe outlet 201 to a container of fluid (such as a drug or other fluid) that is to be dispensed; various methods may be used for this connection but may include a needle or nozzle attached to the outlet 201 of syringe 200. Because fluid flow control apparatus 10 of the present invention does not allow fluid to flow at a high rate from syringe outlet 201 into syringe barrel 203, check valve assembly 210 allows fluid to flow into said syringe. When syringe plunger 202 is retracted to draw fluid into barrel 203, ball 212 shifts (generally in the direction of plunger 202) which allows flow of fluid into syringe barrel 203. After a user has drawn in a desired amount of fluid and stops retracting the plunger, spring 213 in said check valve assembly 210 biases check valve ball 212 onto internal seat 211 of said check valve assembly 210, thereby preventing any flow of fluid through said check valve assembly 210 out of said syringe barrel 203. Flow rate of fluid dispensed by said syringe 200 regulated or controlled by fluid flow control apparatus 10 of the present invention the manner described herein.

Figure 17:
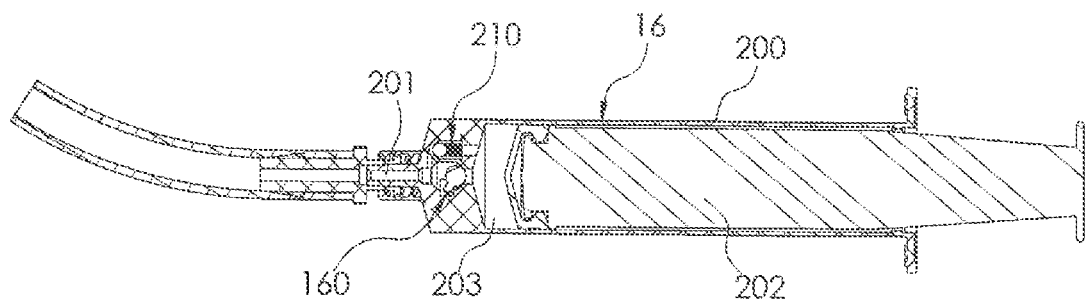
FIG. 17 depicts a side sectional view of a second alternative embodiment fluid flow rate control apparatus of the present invention in a syringe also equipped with a check valve assembly.
Figure 18:
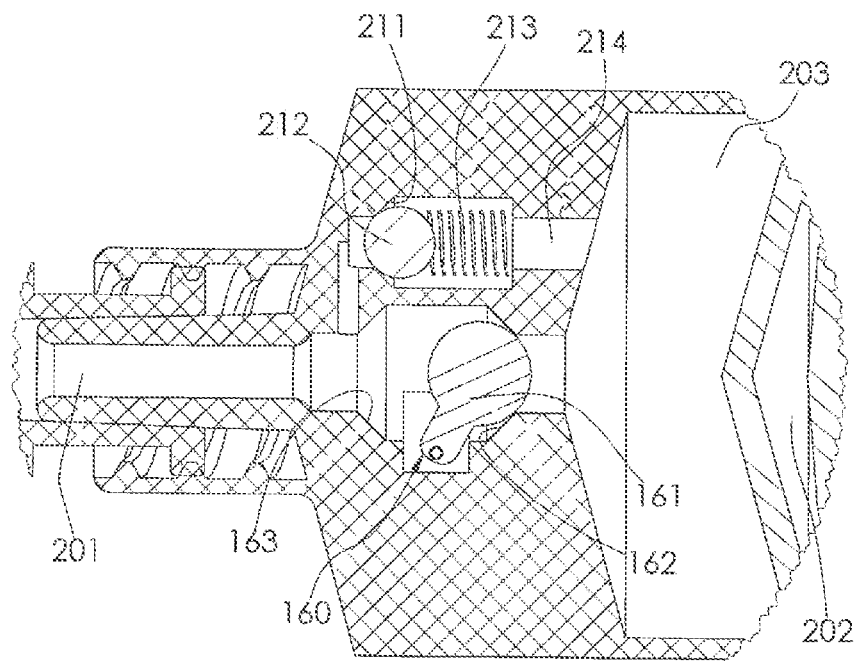
FIG. 18 depicts a detailed sectional view of a portion of the second alternative embodiment depicted in FIG. 17.

FIG. 17 depicts a side sectional view of a second alternative embodiment fluid flow rate control apparatus 16 of the present invention in a syringe also equipped with a check valve assembly 210, while FIG. 18 depicts a detailed sectional view of a portion of said second alternative embodiment fluid flow rate control apparatus 16 depicted in FIG. 17. The second alternative embodiment fluid flow rate control apparatus 16 depicted in FIGS. 17 and 18, comprises an alternative fluid flow rate control apparatus 160 including flapper member 161 generally in place of a ball (such as ball 70 depicted in FIGS. 15 and 16). As depicted in FIGS. 17 and 18, said flapper 161 is initially in a closed position, wherein said flapper 161 blocks fluid flow into barrel 203 during loading of said syringe 200 (before flow is initiated in an opposite direction out of said syringe 200).

Using a spring or other biasing means, said flapper 161 remains biased against inlet seat 162 unless acted upon by a predetermined force imparted in an opposing direction. As with the embodiment depicted in FIGS. 15 and 16, said flapper 161 remains in an open position when flow out of said syringe barrel 203 is maintained at a predetermined (i.e., acceptable) flow rate, but shifts onto outlet seat 163—thereby interrupting or restricting fluid flow through syringe output port 201—if a predetermined maximum fluid flow rate out of said syringe barrel 203 is achieved or exceeded.

Figure 19:
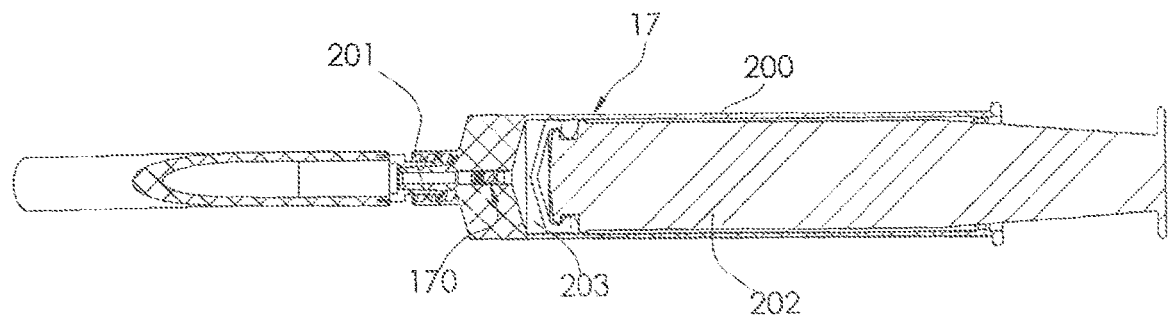
FIG. 19 depicts a side sectional view of a third alternative embodiment fluid flow rate control apparatus of the present invention in a syringe.
Figure 20:
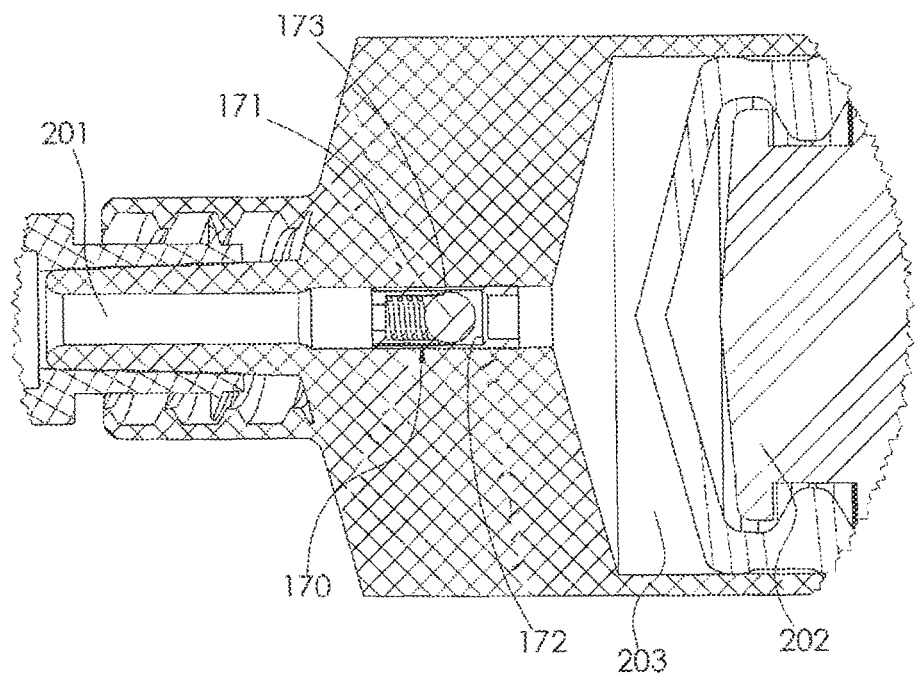
FIG. 20 depicts a detailed sectional view of a portion of the third alternative embodiment depicted in FIG. 19.

FIG. 19 depicts a side sectional view of a third alternative embodiment fluid flow rate control apparatus 17 of the present invention, while FIG. 20 depicts a detailed sectional view of a portion of said third alternative embodiment fluid flow rate control apparatus 17 depicted in FIG. 19. In said third alternative embodiment depicted in FIGS. 19 and 20, a fluid flow control apparatus 170 of the present invention is installed directly into an output flow port 201 or output channel of a syringe 200. An imperfect or non-uniform sealing surface can be incorporated on inlet seat 172 instead of using a check valve assembly (as depicted in first alternative embodiment 15 and second alternative embodiment 16).

In this configuration, fluid can be drawn into syringe barrel 203 during syringe loading operations by providing a path around ball 171 when said ball 171 is disposed on inlet seat 172. The shape and/or configuration of inlet seat 172 allows for a gap or space to be formed between ball 171 and inlet seat 172, whereby fluid can pass said ball 171 and can be easily drawn into syringe barrel 203, while still creating a large enough contact area between ball 171 and inlet seat 172 to prevent overcoming the cracking pressure of the flow control apparatus 170. Inlet seat 172 can be made imperfect by any method that will still retain ball 171 yet create an adequate gap, space or path around said ball 171 to allow fluids to be drawn into syringe barrel 203 using a predetermined pulling force on syringe plunger 202.

After loading, outlet port 201 of syringe 200 can be attached to a system into which syringe 200 will dispense fluid. As a user depresses syringe plunger 202 towards syringe outlet 201, ball 171 in flow control apparatus 170 of the present invention allows fluid to flow from syringe barrel 203 into syringe outlet port 201 and, eventually, to a patient or output receptacle. However, if the flow rate exceeds a predetermined upper flow rate limit, said ball 171 shifts, forming a fluid pressure seal on outlet port seat 173 and interrupting or blocking flow through said outlet port 201. If the aforementioned "imperfect" (that is, not exactly matching the dimensions of said ball 171) outlet port seat 173 is incorporated into the flow control apparatus 170 of the present invention, the user could discontinue applying force to syringe plunger 202 to allow trapped fluid pressure to partially bleed off, and to allow ball 171 to come off of output port seat 173 and to break said fluid pressure seal.

In operation, a user can select a flow control apparatus having a predetermined desired maximum flow rate limit. In a preferred embodiment, multiple devices of the current invention having different maximum fluid flow rate limits can be color-coded, sized or otherwise marked to simplify the identification and selection of said devices. For example, each apparatus having a particular maximum flow rate capacity can have a predetermined, assigned color that will aid in quick and accurate identification verification of a correct device based on the desired maximum fluid flow rate limit of said device even in emergency settings. In medical applications, a user can determine said desired flow rate capacity based particular drug(s) or other substances being administered. Further, in many embodiments, said flow control apparatus can be relatively small, having a length of 1" or less, and can be configured with desired connection members (such as, for example, Luer lock connection members) for easy and effective operational attachment to mating components.

A user can draw a prescribed or desired amount of medicine or other fluid into a conventional syringe. Said user can operationally connect a flow control apparatus of the present invention to the output port or outlet of a syringe. When desired, the user can then operationally attach an output tube to the outlet port of said flow control apparatus of the present invention. In this embodiment, the apparatus of the present invention is beneficially installed or interposed within a fluid flow path formed between said syringe and a patient (or other receptacle), and beneficially controls the flow rate of medicine or other fluid discharged from said syringe.

To administer or dispense medicine or other fluid from said loaded syringe using the fluid flow control apparatus of the present invention, a user can depress a plunger of said syringe at a force that said user estimates will create a desired syringe fluid output flow rate. If said user depresses said plunger with force that creates a syringe output flow rate in excess of said desired flow rate (and above the predetermined flow rate permitted through the flow control apparatus of the present invention), the ball of the present invention shifts to the outlet port seat thereby creating a seal (either full or partial, depending on the embodiment of the present invention), blocking said output port and interrupting or stopping fluid flow through said flow control apparatus (and, ultimately to a patient or receptacle).

When said ball comes in contact with said outlet port seat, said user will typically notice an obvious and nearly-instantaneous change in syringe plunger resistance force. A user may also hear a slight clicking sound of said ball contacting said outlet port seat. When said user observes or senses that said plunger is no longer moving (or moving at the same rate), the user may elect to momentarily stop applying force to the plunger, thereby allowing said sealing ball to release from said outlet port seat as trapped fluid pressure between said ball and said syringe plunger is relieved. Thereafter, the user can resume depressing the syringe plunger.

If the fluid flow control apparatus of the present invention is configured with an "imperfect" outlet port seat—such as a dimple on said seat or bleed off flow channel—as discussed herein, a predetermined volume of fluid will continue to flow past said ball and seat over a predetermined period of time even when said ball is received on said seat, thereby relieving a portion of the fluid pressure acting on said ball. Relief of such fluid pressure allows said ball to move off of said outlet port seat, thereby eventually allowing greater fluid flow rate between said ball and seat. In this configuration, fluid flow through the fluid flow control apparatus is restricted, but is typically not fully interrupted or stopped. When equipped with a fluid flow control apparatus of the present invention, a user pushing on a syringe plunger will administer medicine or other fluid from a syringe, but will not exceed a predetermined maximum flow rate.

The above-described invention has a number of particular features that should preferably be employed in combination, although each is useful separately without departure from the scope of the invention. While the preferred embodiments of the present invention are shown and described herein, it will be understood that the invention may be embodied otherwise than herein specifically illustrated or described, and that certain changes in form and arrangement of parts and the specific manner of practicing the invention may be made within the underlying idea or principles of the invention.

What is claimed:

1. A medicant dispensing apparatus comprising:
   a syringe; and
   a locking adapter comprising;
     a body section having a first flow bore; and
     a first connection means at a first end having a first fluid inlet fluidly connected to the syringe; and
     a second connection means at a second end having a first fluid outlet; and
     a first flow bore between the first fluid inlet and the first fluid outlet; and
     a fluid flow control apparatus positioned within the first flow bore;
       the fluid flow control apparatus further comprising:
         a housing having a first seat and a second flow bore positioned between a second fluid inlet and a second fluid outlet, and
         an end member positioned within the second flow bore having a second seat and a third flow bore between a third fluid inlet and a third fluid outlet, wherein the second seat has at least one dimple; and
         a sealing ball positioned within the second flow bore, wherein the sealing ball contacts the first seat in a closed position and contacts the second seat in an open position; and
         a compression spring positioned within the third flow bore of the end member which biases the sealing ball toward the first position; and
       wherein a first fluid flow path is formed between the housing of the fluid flow control apparatus and the end member when the sealing ball is in the open position allowing fluid flow through the first and second flow bores, and wherein a second fluid flow path is formed between the sealing ball and the end member when the sealing ball is in the open position and is adjacent to the dimple allowing fluid flow through the first, second, and third bores.

2. The medicant dispensing apparatus of claim 1, wherein said first, second, or third fluid outlet is in fluid communication with an inlet of an intravenous medication tube.

3. The medicant dispensing apparatus of claim 1, wherein at least one of the first connection means or the second connection means includes ribs, threads, or protrusions.

4. The medicant dispensing apparatus of claim 1, wherein the first, second, and third flow bores are coaxial.

* * * * *